United States Patent [19]

Wong et al.

[11] 4,237,885
[45] Dec. 9, 1980

[54] DELIVERY SYSTEM WITH MATED MEMBERS FOR STORING AND RELEASING A PLURALITY OF BENEFICIAL AGENTS

[75] Inventors: Patrick S. L. Wong; Bruce B. Pharriss, both of Palo Alto, Calif.

[73] Assignee: Alza Corporation, Palo Alto, Calif.

[21] Appl. No.: 953,480

[22] Filed: Oct. 23, 1978

[51] Int. Cl.³ .............................................. A61M 7/00
[52] U.S. Cl. .................................... 128/260; 156/145
[58] Field of Search ................... 128/127, 130, 213 R, 128/222, 260, 261; 424/19, 22, 16; 264/152, 281, 320–321, 328; 156/48–49, 122, 145, 158, 296

[56] References Cited

U.S. PATENT DOCUMENTS

| | | | |
|---|---|---|---|
| 3,545,439 | 12/1970 | Duncan et al. | 128/260 |
| 3,920,805 | 11/1975 | Roseman | 128/130 |
| 3,991,760 | 11/1976 | Drobish et al. | 128/260 |
| 4,012,496 | 3/1977 | Schöpflin et al. | 128/130 |

*Primary Examiner*—C. Fred Rosenbaum

*Attorney, Agent, or Firm*—Paul L. Sabatine; Edward L. Mandell; Thomas E. Ciotti

[57] ABSTRACT

A delivery system is disclosed. The system is useful for the preprogrammed, unattended delivery of at least one beneficial agent to a pre-selected environment of use. The system comprises (I), a beneficial agent (II), a delivery module comprising, (a) a closed tubular member twined about itself to form a multiplicity of continuous, entwined, mated members, the members having, (b) an internal reservoir for storing agent in an amount for execution of the program, (c) a rate controller which maintains the rate of agent delivered in an effective amount from the members throughout the life of the system, (d) an energy source for transferring agent from the reservoir to the environment, and, (e) a portal for releasing agent from the members to the environment, (III), a platform which integrates the module into a unit sized, shaped and adapted for insertion and retention in the environment, and, (IV) a program which provides for the controlled release of agent to produce the desired beneficial effect over a prolonged period of time.

23 Claims, 5 Drawing Figures

DELIVERY SYSTEM WITH MATED MEMBERS FOR STORING AND RELEASING A PLURALITY OF BENEFICIAL AGENTS

FIELD OF THE INVENTION

This invention pertains to an agent delivery system. The system comprises an agent, a delivery module, a platform and a program that operate as a unit for delivering an effective amount of the agent to an agent receptive environment. More specifically, the invention relates to a system manufactured with a plurality of delivery members resembling each other for delivering one or more agents. The invention also concerns processes for making the system.

BACKGROUND OF THE INVENTION

Devices for delivering a useful agent including drugs are known to the prior art. For example, U.S. Pat. No. 3,545,439 issued to Gordon W. Ducan discloses a medicated annular device designed as a resilient individual ring that can be made from various polymeric materials. The device is used for intravaginally releasing a medicament. The device optionally contains a tension spring for keeping it in the vagina. In U.S. Pat. No. 3,920,805 patentee Theodore J. Roseman discloses a solid, polymeric device that has a nonmedical central core and an encircling medicated coating made of a polymer. The device releases drug by diffusion and in a preferred embodiment, the device is ring-shaped with a flat tensioning spring molded in the nonmedicated central core. In U.S. Pat. No. 3,991,760 patentees James L. Drobish and Thomas W. Gougeon disclose a device for use in the vaginal canal. The device consists of a plurality of individual containers connected by a seal fin in a plane perpendicular to the plane of the device. The containers have a microporous wall for releasing a surfactant in the vagina. In U.S. Pat. No. 4,012,496, patentees Gisela Schopflin, Gerhard Laudahn, Barbara Mirhe, Heidemane Hartmann and Fredt Windt disclose a device having a major and minor portion. The major portion consists of a ring having at least a portion of its surface adapted to mate with a minor medicament containing segment. The minor segment fits into a pocket-like indentation in the major portion. The minor segment releases medicament in the vagina channel over time.

While the above-described devices are useful for certain applications and environments, there are serious disadvantages frequently associated with these devices that limit their use. For example, one disadvantage is the devices may have many parts made of different materials which require individual molding and curing fabrication procedures to make the devices. These fabrication procedures tend to restrict the shape of the devices and the use of different parts tends to produce rigid devices. The devices usually are designed for housing a single agent and the amount of agent that can be loaded into the devices is limited by its restricted design and parts. Also, the devices have a constant release surface and they cannot be adjusted for different needs. Those versed in the delivery art will recognize that if devices can be provided that are essentially free from the above tribulations, such devices would be a valuable advancement and a useful improvement in the delivery art.

PURPOSES OF THE INVENTION

Accordingly, it is an immediate purpose of this invention to provide an improved delivery system that is simple in construction for the controlled and continuous delivery of a beneficial agent over a prolonged period of time.

Yet another purpose of this invention is to provide a delivery system manufactured in the form of a device, that is easy to manufacture, and can release one or more useful agents at meaningful rates over a prolonged period of time.

Still another purpose of the present invention is to provide a delivery system that is flexible, can have low to high agent loading, and which system can deliver the agents at a controlled and useful rates over prolonged periods of time.

Another purpose of the instant invention is to provide a delivery system manufactured with biologically compatible materials that has an increased surface area for releasing a drug to a biological environment.

Yet another purpose of the invention is to provide a device that is economical to make, can be replaced after short and long periods of time, and has a rate of flux that can be prechosen by preselecting the materials used for making the device.

Other purposes, features, aspects and advantages of the invention will be more apparent to those versed in the art from the following detailed specification, taken in conjunction with the accompanying figures and claims.

SUMMARY OF THE INVENTION

This invention concerns a system useful for delivering a beneficial agent to an environment of use. The system comprises a wall surrounding and forming a reservoir containing the beneficial agent and optionally an inner mass transfer conductor. The wall defines a primary geometric configuration and a plurality of auxiliary accompanying members having the primary configuration and threaded around the primary configuration. The wall and the conductor are permeable to the passage of agent, but the permeability of the wall to the passage of agent is lower than through the conductor. Since the permeability through the wall is lower, passage through the wall is the rate determining flux for releasing an effective amount of agent from the operable system over time.

BRIEF DESCRIPTION OF THE DRAWINGS

In the drawings, which are not drawn to scale, but are set forth for illustrating various embodiments of the invention, the figures are as follows.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
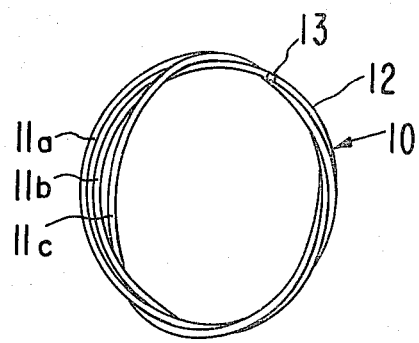
FIG. 1 is a top view illustrating a delivery system provided by the invention and manufactured with a multiplicity of entwining delivery members.

Turning now to the drawings in detail, which are examples of systems that can be used for releasing a beneficial agent, and which examples are not to be construed as limiting the invention, one embodiment thereof is seen in FIG. 1 identified by the numeral 10. The phrase "delivery system" as used herein refers to a system manufactured in the form of a delivery device, which provides a pre-programmed, unattended delivery of an agent, at a controlled rate, and for a time period established to meet a specific need.

System 10, as seen in FIG. 1, comprises a multiplicity of members identified as 11a, 11b and 11c, which are entwined around each other. The members possess a similar geometric configuration that imparts both shape, structure and design to system 10. The phrase "a multiplicity of members", as used for the purpose of this invention, means at least two members, and in a presently preferred embodiment it consists essentially of three to ten members. Members 11a, 11b and 11c originate from a common, continuous wall material 12 that surrounds and defines as internal reservoir, not seen in FIG. 1. Wall 12 in the depicted embodiment is a tubular structure with a pair of ends united at a loci by a connector 13 to form closed, delivery system 10. Tubular structure 12 is initially shaped to a preselected design that one end, or optionally both ends of the tube are threaded around the initial shaped design to form a collection of members identified as 11a, 11b and 11c. Connector 13 in one embodiment is a plug made of a solid material having outside dimensions that correspond to the inside dimensions of the members of system 10 and it unites the ends of wall 12 to form a closed system. In another embodiment connector 13 can be a tube, or the ends of wall 12 can be adhesively joined or heat united to form closed system 10.

Figure 2A:
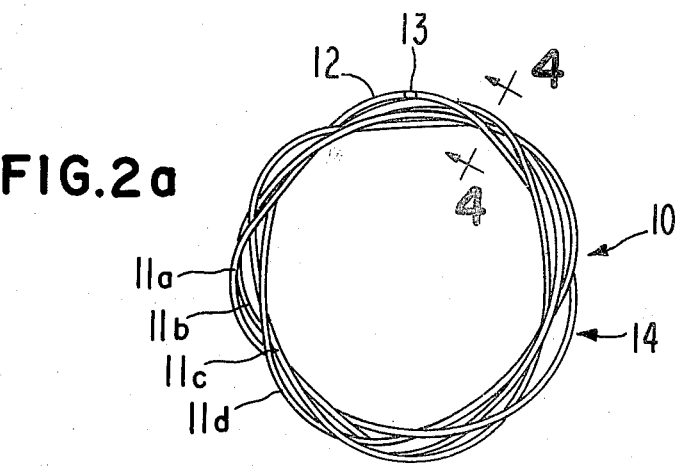
FIG. 2a is a top view of another delivery system made with a greater number of like-shaped members sized, shaped and adapted for insertion and retention in an environment of use.
Figure 4:
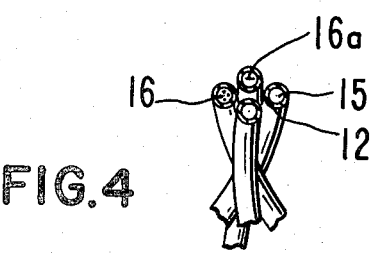

System 10, as seen in FIG. 2a, is adapted, shaped, sized and structured for easy placement and comfortable retention in an environment of use for delivering a beneficial agent to the target receptor site. System 10 can be defined as a delivery module 14, which module is essentially the body of system 10. The delivery module comprises: (a) a plurality of members consisting essentially of members 11a through 11d, with one of said members the main member embracing the preselected geometric configuration, and the remaining members characterized as auxiliary members intertwined around the main member; (b) a reservoir or internal space 15, as seen in FIG. 4, which is a cross-section taken through 4—4 of FIG. 2, for storing an amount of agent, seen as dots 16, required for execution of the prescribed agent program; (c) a rate controller or the wall 12 of the module that surrounds and forms internal reservoir 15, which wall 12 maintains the prescribed rate of agent released throughout the life of system 10; (d) an energy source 16, or the concentration of agent in reservoir 15 that provides the driving energy for transferring agent 16 from a higher concentration in reservoir 15 to rate controller 12 for release to the environment of use; (e) an optional inner mass transfer conductor, dash 16a in FIG. 4, usually a liquid-like material that provides a means for storing and supplying agent to the wall in reservoir 15; and (f) a portal which in this invention is rate controller wall 12 that provides an exit from the module to the exterior of the system.

Figure 2B:
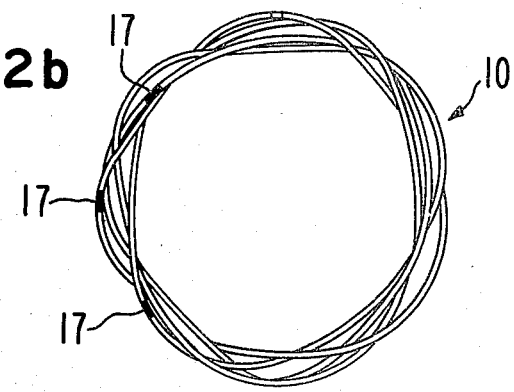
FIG. 2b is a view similar to FIG. 2a illustrating the system with means for housing more than one agent separated from each other within the same system.

In FIG. 2b, system 10 of FIG. 2a is manufactured with means for storing and releasing more than one agent. The means consists of spaces 17 placed in one or all of members 11a through 11d for forming a multiplicity of internal reservoirs, number 15 in FIG. 4. The spaces can be near or distant from each other for governing the space in a reservoir, and correspondingly the amount of different agents therein. The spaces are made of various materials, usually polymers that are impermeable to the passage of agents and conductors for preventing mixing of agents from neighboring reservoirs. The spaces have a cross-sectional area that correspond to the cross-sectional area of the reservoir for forming a multi-reservoir, multi-agent device.

Figure 3:
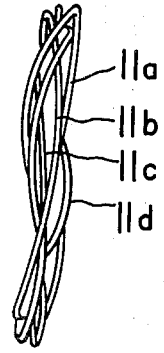
FIG. 3 is a side view of the delivery system of FIG. 2a depicting the multiplicity of inter-threaded, like members comprising the system; and, FIG. 4 is a cross-section, opened view of FIG. 2a through numbers 4—4 illustrating the internal reservoir of the system.

FIG. 3 is a single, side view of FIG. 2a presented for showing the multiplicity of revolutions forming a plurality of continuously entwined members that comprise system 10.

System 10 is an integral unit adapted as a platform that can embrace many shapes. That is, the system can have various continuous, curved shapes, such as annular or ring, oval, ellipse, toroidal, triangular, square, figure eight shaped, and the like. The dimensions of the system will vary depending on the environment and the shape used for delivering the agent. The system can be shaped for use in environments such as aquariums, laboratory facilities, and for delivering an agent to a host. The term host generically includes animals, which latter term includes warm-blooded mammals, humans, primates, farm and laboratory animals. The system can be adapted for implantation, insertion or positioning in body cavities and passageways. The dimensions of the system will vary depending on the host and the shape used for delivering the agent. For example, in a presently preferred embodiment the system is designed as an annular ring for placing in a vagina. In this embodiment the device will have a maximum dimension measured from one loci on the wall of one member to a distant loci on the wall of a member of from 0.4 cm to 20 cm, with presently preferred devices exemplified by an annular shaped system of from 0.5 cm to 16 cm, with general dimensions for various hosts as follows: human 4 cm to 12 cm; sheep 2 cm to 7 cm; dogs 0.5 cm to 5.0 cm; swine 2 cm to 7.5 cm; Rhesus monkey 2 cm to 4 cm; household cats 0.4 cm to 4 cm, and dairy cattle 5 cm to 12 cm. The total diameter of all members measured through the total average cross-section, as represented by 4—4, generally is about 4 mm to 30 mm.

DETAILED DESCRIPTION OF THE INVENTION

In accordance with the practice of this invention, it has now been found the above-described systems can be made from polymeric materials manufactured in tube shape. The wall 12 of the manufacture is a rate controller for releasing agent over time. The materials selected for use are substantially free of any adverse effect on an animal host. Since the body passageways are lined with an extremely delicate tissue, it is essentially the materials forming system 10 do not adversely effect the host. The materials used for the purpose of the invention are biologically compatible materials set forth below. By compatible is meant the materials are acceptable within the animal body. The materials do not break down, there is no absorption, and there isn't any deleterious action on the sensitive tissues in the area of placement and retention over a prolonged period of time.

Exemplary wall forming materials that do not adversely effect the environment of use include olefins and vinyl-type polymers, carbohydrate-type polymers, synthetic condensation-type polymers, natural and synthetic rubber-type polymers, organo-silicon polymers, preformed microporous-type polymers and other diffusion release-type polymers. Specific polymers include polyethylene, ethylene-vinyl acetate copolymer, copolymers of polystyrene, polyvinylcarbazole, (polyvinyl acetate, polyarcrylate, segmented (polyether-coester) polyester, cellulose, polyamide, polyethylene terephthalate, polyurethane, microporous polyurethane, polysiloxane, and the like. The polymers are known to the art in *Handbook of Common Polymers*, by J. R. Scott and W. J. Roff, 1971, published by The Chemical Rubber Company, Cleveland, Ohio; and in *Handbook of Plastics and Elastomers*, edited by Charles A. Harper, 1975, published by McGraw-Hill Company, New York.

The expressions "beneficial agent" and "useful agent" as used herein broadly includes compounds, composition of matter, or mixtures thereof that can be delivered in effective amounts to produce a beneficial and useful result. The active agents 16 include pesticides, herbicides, algicides, germicides, rodenticides, insecticides, antioxidants, plant growth promoters, plant growth inhibitors, preservatives, disinfectants, sterilization agents, catalysts, chemical reactants, fermentation agents, food supplements, nutrients, cosmetics, drugs, vitamins, sex sterilants, fertility inhibitors, fertility promoters, air purifiers, micro-organism attenuators, and other agents that benefit the environment of use, and the habitat.

In a presently preferred embodiment, the active agent is an antifertility steroid. The steroids include progestational steroids that have antifertility properties and estrogenic substances that have antifertility properties. These substances can be of naturally occurring or synthetic origin and they generally possess a cyclopentanophenanthrene nucleus. The term progestational substance as used herein embraces progestogens, which latter term is used in the pharmaceutically acceptable steroid art to generically describe steroids possessing progestational activity, and the former also includes progestins, a term widely used for synthetic steroids that have progestational effects. The active antifertility progestational agents that can be used to produce the desired effects in mammals, including humans and primates, are without limitations: pregn-4-ene-3,20-dione; progesterone; 19-nor-pregn-4-ene-3,20-dione; 17-hydroxy-19-nor-17α-pregn-5(10)-ene-20-yn-3-one; 17-ethinyl-17-hydroxy-5(10)-estren-3-one; 17α-ethynyl-19-norestosterone; 6-chloro-17-hydroxypregna-4,6-diene-3,20-dione; 17α-hydroxy-6α-methyl-17(1-propynl)androst-4-ene-3-one; 9α,10α-pregna-4,6-diene-3,20-dione; 17-hydroxy-17α-pregn-4-en-20-yne-3-one; 19-nor-17α-pregn-4-en-20-yn-3,17-diol; 17-hydroxy-pregn-4-ene-3,20-dione; 17α-hydroxyprogesterone; 17-hydroxy-6α-methylpregn-4-ene-3,20-dione; 17-hydroxy-19-nor-17α-pregn-4-en-20-yn-3-one or norethindione; 13-ethyl-17-hydroxy-18,19-dinor-17α-pregn-4-en-20-yn-3-one or norgestrel; norethindrone; norethynodrel; norgesterone; norgestrienone; and mixtures thereof, and the like.

The term estrogenic and estrogenic antifertility agents as used herein also include the compounds known as estrogens that possess antifertility properties including α-estradiol; α-estradiol-3-benzoate; 17α-cyclopentanepropionate estradiol; 1,3,5,(10)-estratriene-3,17α-diol dipropionate; estra-1,3,5(10)-triene-3,17α-diol valerate; estrone; ethinyl estradiol; 17-ethinyl estradiol-3-methyl ether; mestranol, 17-ethinyl estradiol-3-cyclopentoether estroil; mixtures thereof, and the like. Generally, the system will contain from 25 nanograms to 5 grams of progestational or estrogenic steroid for release at a rate of 0.05 micrograms to 50 milligrams per day, and in a presently preferred range of 0.5 milligrams to 6.0 milligrams per day. Generally, the system can be used for a period of 1 day to 1 year, or longer. The above steroids and their dose amounts for humans are known in *Drill's Pharmacology in Medicine*, edited by DiPalma, J. R., 1965, published by McGraw-Hill Book Company, New York, and in *Pharmacological Basis of Therapeutics*, by Goodman and Gilman, 4th Edition.

The useful agent can be present in the form of accepted derivatives, such as their hydroxy or keto groups can be in a derivative form for the present purpose. These forms should easily convert to the parent agent upon its release from the device by activities such as enzymatic transformation, pH assisted hydrolysis, metabolic conversion, and the like. The derivatives also can be used to control the solubility of the agent in the liquid core and to assist in metering the agent from the device. Suitable derivatives include ethers, esters, amides, salts, and the like.

Exemplary inner mass transfer conductors, 16a, that are suitable for use with the agent in the reservoir are generically liquid and liquid-like carriers that can transfer the agent to the wall of the device. These carriers are permeable to the passage of agents and they include liquids capable of forming a liquid carrier wall interface at the inner surface of the wall. Typical conductors include a member selected from the group consisting essentially of alkylene glycols, dialkylene glycols, poly(alkylene glycols), vegetable oils, animal oils, fruit oils, nut oils, marine oils, mineral oils, sylvan oils, organic oils, inorganic oils, saline, buffers, aqueous media, aqueous media such as water mixed with poly(alkylene glycols) including poly(ethylene glycols) having a weight of 400 to 6000, poly(propylene glycol) having a molecular weight of 500 to 2000, polyoxyethylene/polyoxy propylene block copolymers having molecular weight of 1000 to 20,000, glycerol polysorbate 80, and the like. Examples of carriers are known to the art in *Pharmaceutical Sciences* by Remington, 1970, published by Mack Publishing Company, Easton, Pennsylvania.

Connector 13 used for joining the two ends of member 11 is made from a material that can join the ends, and does not adversely effect the agent, the member and the environment of use. The connector generally is a polymer material such as polyethylene, polyproplyene, nylon, polytetrafluoroethylene, and the like. The connector can be a solid or a tube made from these materials.

The ends of member 11 can be adhesively united to form a closed system. The term adhesive as used herein means a substance that holds the ends together by surface attachment. The adhesive and ends join in intimate contact achieved by the adhesive wetting the ends. Adhesives suitable for the present purpose include natural adhesives and synthetic adhesives. Typical adhesives include animal, nitrocellulosic, polyamide, phenolic, amino, epoxy, isocyanate, acrylic, silicate, silicone, organic adhesives of the membrane polymers, and the like. The adhesives are known to the art in *The Encyclopedia of Chemistry*, Second Edition, edited by George L. Clark and Gessner G. Hawley, 1966, published by Van Hostrand Reinhold Company, Cincinnati, Ohio.

DETAILED DESCRIPTION OF FABRICATION

The systems used for the purpose of this invention are fabricated as follows: first, a section of ethylene-vinyl acetate copolymer tubing having a vinyl acetate content of 25% is washed with water for 32 to 42 hours, and then dried in air at room temperature. Then the tubing is cut into an appropriate length and shaped like a ring, as seen in FIG. 1. The system is shaped by forming a primary ring and threading the ends of the tube around the primary ring to form the auxiliary rings. Next, a connector consisting of a solid polymeric polyethylene plug, having an outside diameter equivalent to the inside diameter of the primary tube, is very lightly dampened with an organic solvent, methylene chloride, and inserted into one end of the tube with a portion remaining for insertion into the other end of the tube. This dual insertion joins the opened tube at its two ends, thereby forming a closed system. The system is filled with agent by injecting an agent carrier mixture into the reservoir of the system through a needle admitted into the reservoir. The filling is continued until all of the air in the reservoir is displaced through an outlet needle admitted into the system. This procedure completely fills the reservoir. Finally, the needle punctures are sealed with a little methylene chloride. Reservoir 15 is filled with progesterone in silicone fluid having a molecular weight of 2500, 50% weight/weight.

An additional system 10 is prepared having a toroidal shape and consisting of a main member and three auxiliary members by inserting a portion of a hollow sleeve tube into one end of the main tube and then inserting the remaining portion of the inner, polymeric sleeve tube into the free end of the main tube. The main and auxiliary members are prepared from butadiene-styrene block copolymer. The sleeve tube is made from low density polyethylene. The copolymer has a wall thickness of 0.5 mm and an internal diameter of 1.5 mm. The average outside diameter for the four inter-threaded members is about 8.8 mm, and the average diameter from a curvature of a member to the distant curvature of a member is about 45 mm. The reservoir is charged with 35% progesterone and 65% polyoxyethylene/polyoxypropylene copolymer having a molecular weight of 3000.

Delivery systems comprising (1) a microporous polyurethane multi-membered, interwound system are made by abutting and sealing the ends with a solvent based adhesive having highly reactive isocyanate groups for facilitating good adhesion of the polymeric ends; and (2) a thermoplastic rubber by ultrasonically welding abutting ends, or by uniting abutted ends in the presence of heated air.

A different delivery system housing three different agents is manufactured as follows: first, a spacer made of an agent impermeable polymer is inserted into a 70 cm length of tube and pushed to the mid-point, thereby forming two segments. Next, 20 cm of each segment from the midpoint are filled with different agents and then distant spacers are inserted into the segments to the agent filled areas forming two reservoirs. The two end segments then are filled with a like agent from the distant spacers to the ends of the tube. Then, the tube is held at its midpoint again forming the two segments that are curved into a first ring-shaped member having a diameter of about 5 cm. Next, one segment is threaded around the ring three times and the other segment threaded in a like manner forming a multi-membered ring-shaped system. The ends of the system are joined by ultrasonic welding procedure. Ultrasonic welding procedures acceptable for the present purposes are described in *Encyclopedia of Polymer Science and Technology*, Vol. 9, page 152, Vol. 12, pages 721 to 724, and Vol. 14 pages 116 to 124, published 1968, by John Wiley and Sons Inc., New York.

Systems containing norethisterone can be placed in the vagina of fertile women where they will be well-received by the vagina. The systems are preferably placed between the rear endometrial wall of the vagina and the upper end of the pubic bone. In this place, the medicating system releases a contraceptively effective amount of steroid each day to yield the intended effect.

It will be understood by those versed in the art in the light of the present specification, drawings and the accompanying claims, the invention makes available to the art both a novel and useful system for delivering agents to produce predesired effects; and, the rate of release from these systems can be controlled to produce these effects. It will be further understood by those versed in the art that many and different embodiments of this invention can be made without departing from the spirit and the scope of the invention. Accordingly, it is to be understood the invention is not to be construed as limited, but it embraces all equivalents inherent therein.

We claim:

1. A system for delivering a drug to a vagina, said system comprising:
    (a) a body sized, shaped and adapted for easy placement and comfortable retention in the vagina, said body comprising;
    (b) a wall surrounding and encompassing an internal reservoir;
    (c) a pair of ends formed integral with the wall and joined to make a closed curved wall, said latter wall circumscribing;
    (d) a multiplicity of entwined revolutions;
    (e) a drug in the reservoir; and,
    (f) wherein, when the system is in the vagina, the system delivers an effective amount of drug at a controlled rate over a prolonged period of time to produce the desired drug effect.

2. The system for delivering the drug to the vagina according to claim 1 wherein the multiplicity of entwined walls increases the drug delivery surface area of the system per unit volume.

3. The system for delivering the drug to the vagina according to claim 1 wherein the multiplicity of entwined walls each define a reservoir with a different drug therein.

4. The system for delivering the drug to the vagina according to claim 1 wherein the reservoir houses a carrier for the drug, and the circumscribing wall defines a multiplicity of entwined rings.

5. The system for delivering the drug to the vagina according to claim 1 wherein the entwined system is toroidal-shaped.

6. The system for delivering a drug to the vagina according to claim 1, wherein the drug is a member selected from the group consisting of progestational and estrogenic steroids, and mixtures thereof.

7. The system for delivering a drug to the vagina according to claim 1 wherein the drug is a steroid selected from the group consisting of norethindrone, norgestrel, norethynodrel, norgesterone, norgestrienone, progesterone, and mixtures thereof.

8. The system for delivering a drug to the vagina according to claim 1 wherein the drug is a steroid selected from the group consisting of menstranol, ethynyl estradiol,α-estradiol, α-estradiol-3-benzoate.

9. The system for delivering a drug to a vagina according to claim 1 wherein the reservoir houses an inner mass transfer conductor selected from the group consisting of alkylene glycol, dialkylene glycol, poly(alkylene glycol), vegetable oil, animal oil, fruit oil, nut oil, marine oil, mineral oil, sylvan oil, organic oil, inorganic oil, silicone oil, saline, buffers, aqueous media, polyoxyethylene-polyoxypropylene copolymer, glycerol polysorbate, and the like.

10. The system for delivering a drug to a vagina according to claim 1 wherein the wall is formed of a material selected from the group consisting of olefins and vinyl polymers, rubber polymers, silicon polymers, microporous polymers, diffusion polymers, polyethylene, ethylene-vinyl acetate copolymers, polyether-ester polymer, and cellulose.

11. A device for delivering a useful agent at a controlled rate to an agent receptive environment of use, said device comprising:
   (a) A curved wall member surrounding and defining an internal hallowed reservoir, said member consisting of:
   (b) a multiplicity of continuously entwined curves around the member;
   (c) a pair of ends formed integral with the wall and joined to make a closed device,
   (d) an agent in the reservoir; and wherein,
   (e) the device is sized and adapted for placement and retention in the environment of use for delivering the agent thereto over a prolonged period of time:

12. The device for delivering the agent at a controlled rate to the environment of use according to claim 11 wherein the multiplicity of entwined curves are revolutions around the member and the revolutions define a plane through the member.

13. The device for delivering the agent at a controlled rate to the environment of use according to claim 11 wherein the revolutions around the member forms a multiplicity of intertwined ring-shaped members.

14. The device for delivering the agent at a controlled rate to the environment of use according to claim 11 wherein the revolutions around the member forms a multiplicity of intertwined toroidal-shaped members.

15. In a process for manufacturing a device adapted for delivering a beneficial agent to an environment of use, said process consisting essentially of the steps of:
   (a) cutting a tube of a polymer to a preselected measured length having a first and second end;
   (b) shaping a part of the tube to a preselected, geometric sized device; the improvement consisting essentially of:
   (c) intertwining the remaining part of the tube around the shaped, sized design in a multiplicity of revolutions to form a plurality of continuously entwined members having a shape resembling the design;
   (d) joining the first and second ends to form a closed device having an internal reservoir for storing a beneficial agent;
   (e) positioning on the device an inlet means and an outlet means spaced apart from each other for communicating with the reservoir and the exterior of the device;
   (f) admitting agent through the inlet means into the reservoir and releasing air in the reservoir through the outlet means; and,
   (g) removing both means and sealing the device housing the agent for delivering the agent at a controlled rate over a prolonged period of time.

16. The process for manufacturing the device for delivering a beneficial agent to the environment of use according to claim 15 wherein the entwined members have a shape and design corresponding to the preselected design.

17. The process for manufacturing the device for delivering a beneficial agent to the environment of use according to claim 15 wherein the ends are joined by inserting into the first end of the tube a pair of a polymeric solid plug having an outside diameter equivalent to the inside diameter of the tube, and then inserting the other pair of the plug into the second end of the tube thereby joining the tube at its ends to form the device.

18. The process for manufacturing the device for delivering a beneficial agent to the environment of use according to claim 15 wherein the process includes heating the ends and contacting said heated end to form the closed device.

19. In a process for fabricating a device that delivers a beneficial agent to an environment of use, said process consisting of the following steps:
   (a) cutting a tube of polymer to a preselected known measurement to provide a length of tube having a pair of ends;
   (b) shaping a section of the length of tube to form part of a predesigned, geometric configuration, while keeping the remaining part of the length of tube available for forming the rest of the device, the improvement comprising;
   (c) threading the remaining part of the length of tube around the configuration in a number of turns to form a multiplicity of members having a shape corresponding to the shape of the configuration;
   (d) bonding together the ends by applying an adhesive to one end and then joining the ends together to form a closed device having an internal reservoir;
   (e) positioning on the device an inlet means and an outlet means spaced apart from each other for communicating with the reservoir and the exterior of the device; and,
   (f) charging agent through the inlet means into the reservoir while venting gas from the reservoir through the outlet means and sealing their position on the device, thereby providing a device housing agent for delivering it at a controlled rate over a prolonged period of time.

20. A process for forming an article of manufacture which manufacture is sized, and shaped as a device useful for releasing a beneficial agent to an agent receptive site, said process consisting essentially of the following steps:
   (a) providing a main tube of a polymer with a known length and having a first and second end;

(b) shaping a section of the main tube to define a prechosen geometric configuration, while keeping the remaining section of the main tube accessible for forming the rest of the device, the improvement consisting of:

(c) twining the remaining section of the main tube around the configuration a plurality of turns to form a multiplicity of elements possessing a shape corresponding to the shape of the configuration; and, (d) inserting a portion of a subservient tube having a length less than the length of the main tube and exterior dimensions approximating the interior dimensions of the main tube into an end of the main tube, and then inserting the remaining portion of the subservient tube into the other end of the main tube to form the device with an internal reservoir for housing a beneficial agent;

(e) placing on the device inlet and outlet ports that communicate with the exterior of the device and the reservoir;

(f) admitting agent through the inlet port into the reservoir while venting reservoir gas through the outlet port; and, (g) removing the ports thereby providing a device filled with agent for delivery at a controlled rate over a prolonged period of time.

21. The process for forming the article of manufacture according to claim 20 wherein the subservient tube is a sleeve and is adhesively held in the main tube.

22. The process for forming the article of manufacture according to claim 20 wherein the main tube and the subservient tube are joined through the application of a solvent that unites the tubes into an integral device.

23. A process for manufacturing a device housing a drug and a carrier, for delivering the drug to an animal, said process comprising the steps of: shaping a tube to a preselected design; interwining the tube around itself to form a multiplicity of interwined members; closing the tube to form a device with an internal reservoir; and injecting a drug and a carrier into the reservoir to for the device housing the drug and carrier.

* * * * *